United States Patent [19]

Sharpless et al.

[11] 4,391,283

[45] Jul. 5, 1983

[54] INCENTIVE SPIROMETER

[75] Inventors: Edward N. Sharpless, Somerville; Marvin Gordon, East Winsor; Joseph Lichtenstein, Colonia, all of N.J.

[73] Assignee: Whitman Medical Corporation, Clark, N.J.

[21] Appl. No.: 247,097

[22] Filed: Mar. 24, 1981

[51] Int. Cl.³ .............................................. A61B 5/08
[52] U.S. Cl. .................... 128/725; 128/727; 272/99
[58] Field of Search ............................. 128/725–728, 128/718–720; 272/99; 73/248, 249

[56] References Cited

U.S. PATENT DOCUMENTS

| | | | |
|---|---|---|---|
| 3,669,097 | 6/1972 | Fitz | 128/728 |
| 3,695,608 | 10/1972 | Hanson | 128/725 X |
| 3,720,202 | 3/1973 | Cleary | 128/727 |
| 3,754,546 | 8/1973 | Cooper | 128/727 |
| 3,802,417 | 4/1974 | Lang | 128/716 |
| 3,923,043 | 12/1975 | Yanda | 128/728 |
| 4,025,070 | 4/1976 | McGill et al. | 272/99 |
| 4,060,074 | 11/1977 | Russo | 128/725 X |
| 4,086,918 | 5/1978 | Russo | 128/725 |
| 4,114,607 | 9/1978 | Russo | 128/725 |
| 4,138,105 | 2/1979 | Hunger et al. | 272/99 |
| 4,170,228 | 10/1979 | Elson et al. | 128/725 |
| 4,183,361 | 1/1980 | Russo | 128/725 |
| 4,241,739 | 12/1980 | Elson | 272/99 X |
| 4,259,951 | 4/1981 | Chernak et al. | 128/725 X |
| 4,299,236 | 11/1981 | Poirier | 272/99 X |

FOREIGN PATENT DOCUMENTS 1385037  2/1975  United Kingdom ................ 128/727

*Primary Examiner*—Lee S. Cohen
*Assistant Examiner*—Angela D. Sykes
*Attorney, Agent, or Firm*—Holman & Stern

[57] ABSTRACT

An incentive spirometer is provided with a mechanism for inhibiting the incentive in response to high flow rate bursts of inhalation so as to promote proper long inhalation efforts by a patient. In one embodiment, the spirometer includes a transparent column located in the inhalation flow path and in which an object is disposed and caused to rise in the column in response to inhalation efforts by the patient. The incentive-inhibiting mechanism may comprise a valve in the rising object which opens in response to excessive flow rate to permit flow through the object and thereby preclude the object from rising. Alternatively, the incentive-inhibiting object may be disposed to admit air into the flow path downstream of the object in response to high flow rate inhalation bursts to thereby reduce the flow rate acting on the object. A variety of embodiments are disclosed. In another embodiment, an indication is provided each time the object is raised to a predetermined height in the column and maintained at the height for a predetermined time, signifying that a minimum volume of air has been inhaled.

29 Claims, 23 Drawing Figures

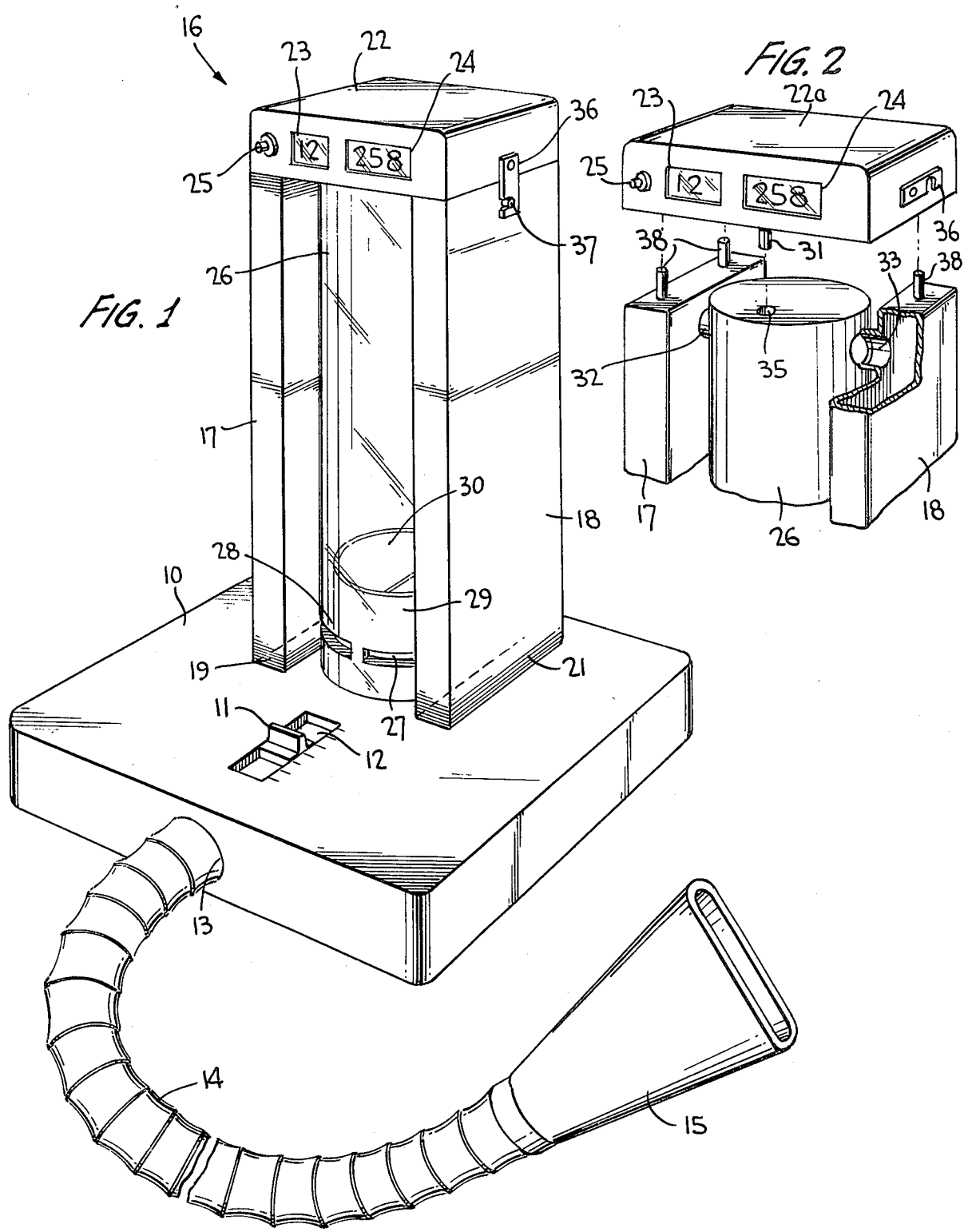

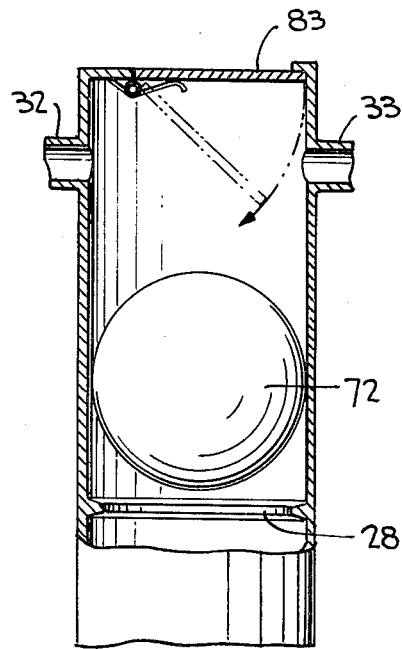
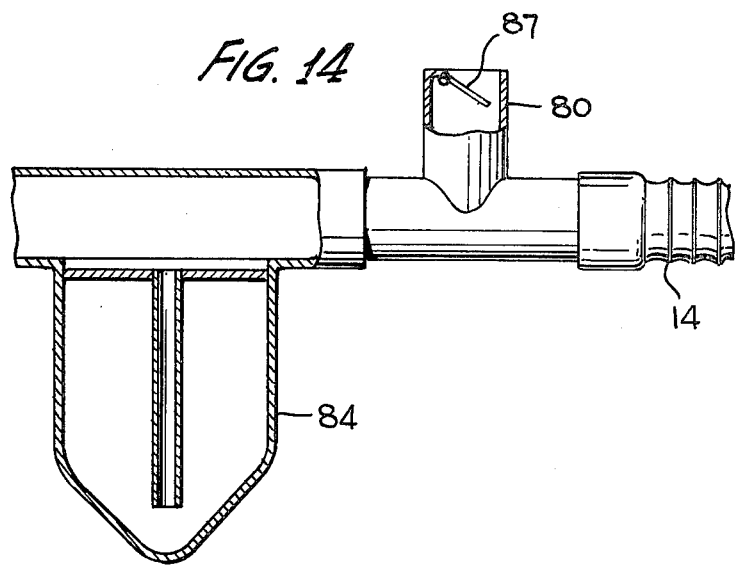
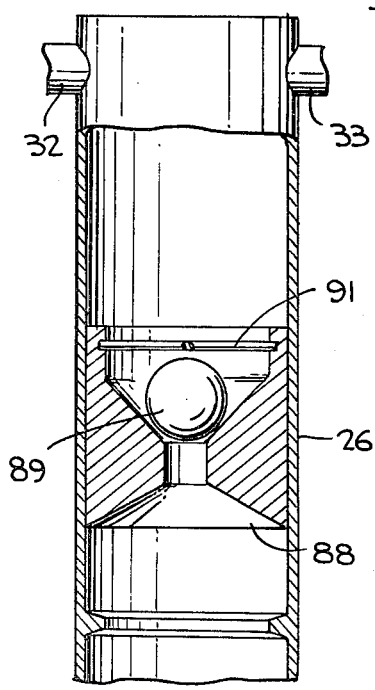
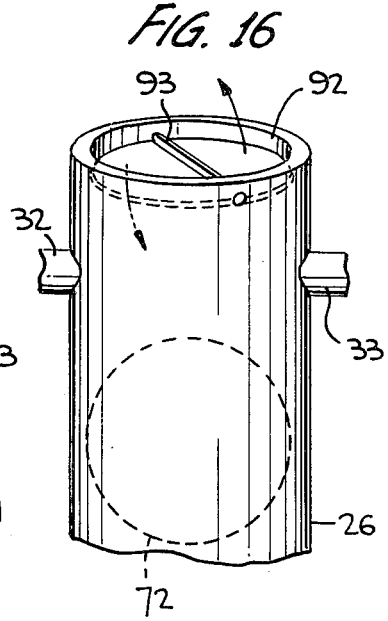
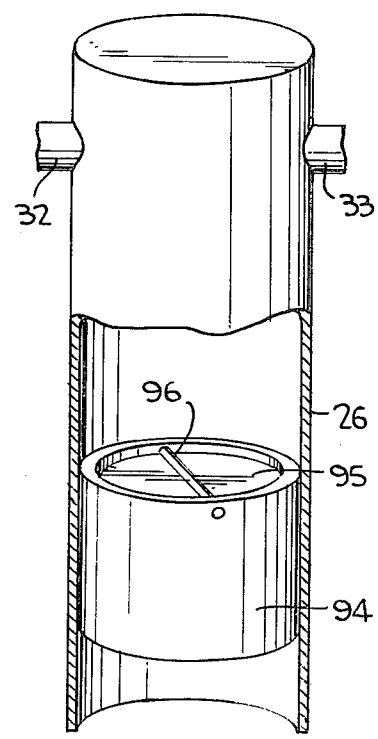

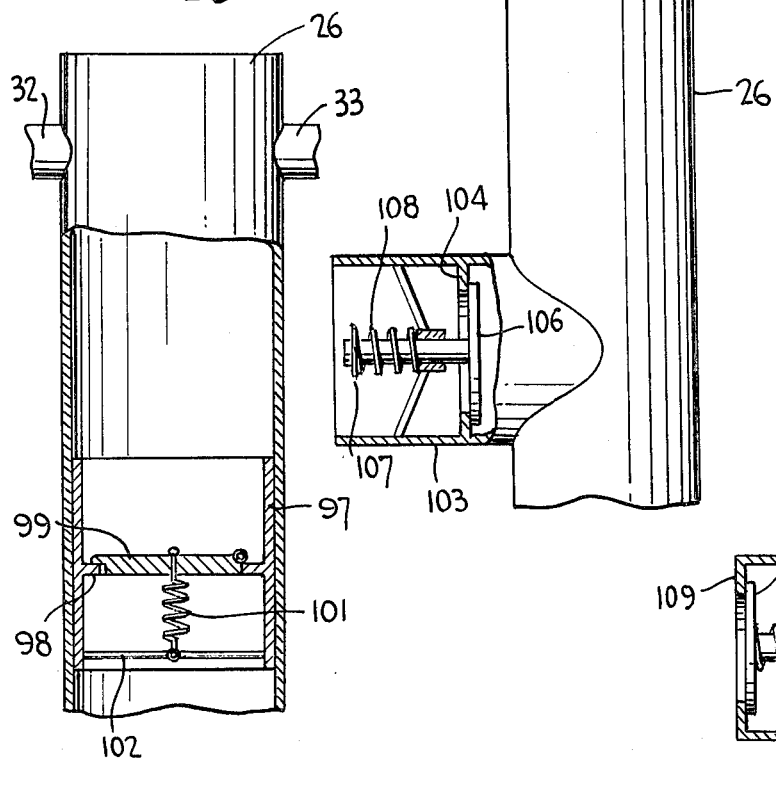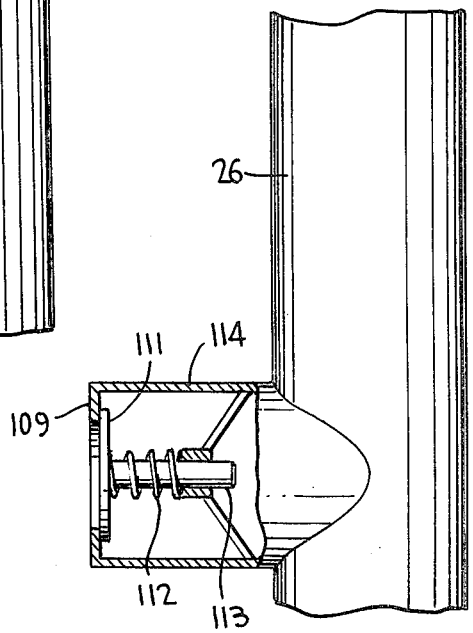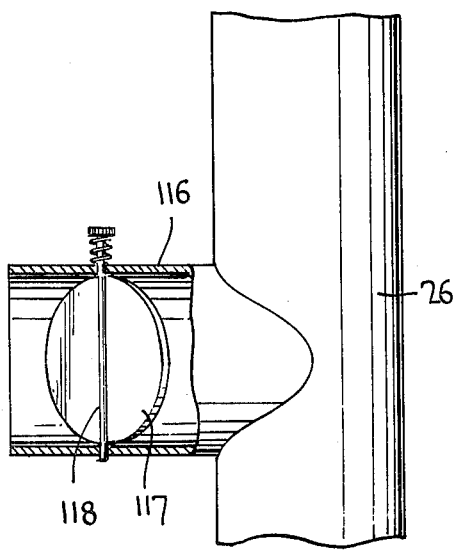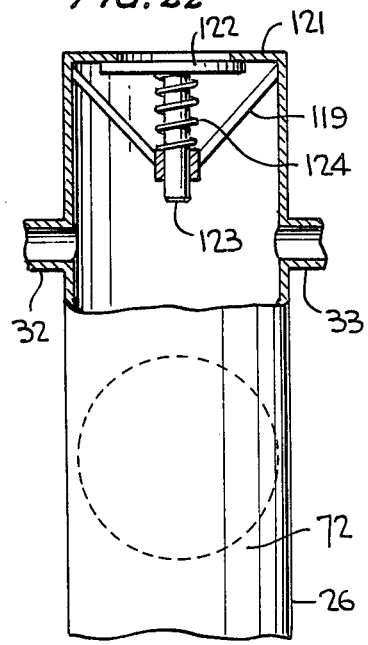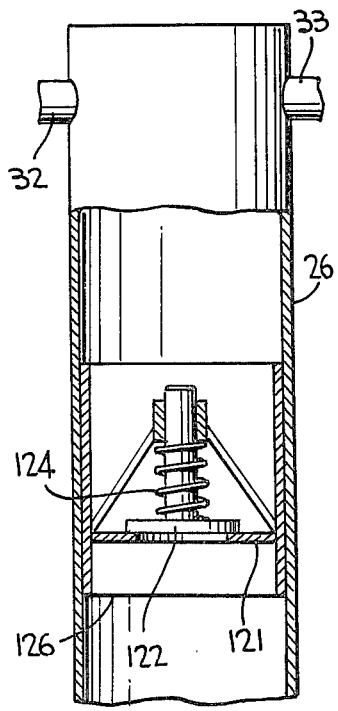

INCENTIVE SPIROMETER

TECHNICAL FIELD

The present invention relates to therapeutic inhalation devices and, more particularly, to improved incentive sprirometers.

BACKGROUND OF THE INVENTION

During the course of post-operative surgery, inhalation therapy is employed to maintain proper functioning of the lungs and to maintain the lungs free of fluid. Incentive spirometers are provided in the prior art which encourage the post-surgical patient to breathe at a desirable flow rate or until a desirable volume has been inhaled. These prior art incentive spirometers are typically constructed such that when a patient inhales through a tube placed in his or her mouth, a visual reward is provided for the patient. In the most common form of incentive spirometers, this visual reward takes the form of a lightweight sphere disposed in a transparent cylindrical column of slightly larger diameter than the diameter of the sphere. The column and sphere are disposed in the inhalation flow path and the flow rate of air inhaled by the patient causes the sphere to rise in the cylindrical column. Incentive spirometers of this type are inexpensively constructed of plastic materials so that they are suitable for disposability after use by each patient. In addition, these devices are easily held and utilized by nearly every patient. Further, only a short training period is required to teach the patient how to correctly use this type of device. The patient is readily interested in achieving the incentive of raising the ball in the column to a prescribed height and holding it there as long as possible by an extended inhalation. One disadvantage of prior art incentive spirometers of the type described is that they include no accurate self-contained means for measuring air displacement. Such an indication is considered quite important in continued therapy for the post-operative patient. Maintaining the sphere at the prescribed height in the cylinder does, in fact, correspond to an inhalation rate which has been prescribed by the therapist for that particular patient. The patient achieves a specific volume of inhalation by holding the inhalation rate for a period of time specified by the therapist; or, more typically, holding the inhalation for as long as the patient is able to sustain such rate. However, in order to interpret this relationship and produce an air displacement volume indication, a means of recording the length of time that the sphere has been held in place must be included. The use of timing devices which are not self-contained in the spirometer tend to complicate the procedure with the result that the patient tends to lose interest.

Another problem with prior art incentive spirometers of the flow rate type resides in the fact that the patient quickly learns how to achieve the incentive by cheating with short, quick inhalation bursts. In other words, the sphere can be raised in the cylinder by sudden bursts of inhalation. The patient, in his or her mind, has achieved the object of the incentive spirometer by moving the sphere some distance with an inhalation; however, the patient has not achieved the results necessary for therapy, namely achieving a long slow inspiratory effort at some prescribed flow rate. The inhalation bursts negate the intended goal of incentive spirometry in three (3) ways: (a) the patient does not achieve a sustained flow rate; (b) the patient does not achieve full use of his or her lungs to provide for normal exchange of gases; and (c) in the extreme case, the patient can hyperventilate while achieving the visual reward of raising the ball with a short burst.

The effort required to raise the sphere in the cylinder in spirometers of the type described is a function of many variables, such as air passage diameters, bends and other restrictions in the passages, mouthpiece design, the size of air inlets, the diameter and mass of the sphere, and the distance which the sphere must rise. There are a variety of prior art devices available, which represent a wide variation in the manner in which incentive is achieved. For example, in one device, a valve is employed to vary the effort required to raise the sphere. In another device, plural spheres are employed, each requiring a faster rate of inhalation to be lifted in a cylinder, and the incentive is for the patient to raise the spheres in sequence. These devices have largely not been successful in requiring the patient to inhale at a gradually increasing flow rate.

It is therefore an object of the present invention to provide an incentive spirometer having a self-contained means of recording the length of time during which an inspiratory incentive is achieved. It is a further object of the present invention to provide such an incentive spirometer which, nonetheless, is sufficiently inexpensive to be disposable.

It is a further object of the present invention to provide an indication each time a patient inhales at least a predetermined minimum volume of air.

It is also an object of the present invention to provide an incentive spirometer having a built-in feature which precludes a patient from achieving the incentive by means of short inhalation bursts.

SUMMARY OF THE INVENTION

In accordance with one aspect of the present invention, an actuator switch is disposed at a prescribed height in a cylinder, usually at the top of the cylinder, and is actuable by an object which can be raised in the cylinder by inspiratory efforts of a patient. This switch is part of an electronic circuit which responds to switch actuation by measuring and recording the time duration as well as the number of occurrences of achieving the incentive of raising the object to the prescribed height in the tube. An occurrence is noted by a visible or audible indication which is provided after the switch has been maintained actuated for at least a predetermined time. If the device is calibrated so that the minimum flow rate required therethrough to actuate the switch is known, the predetermined time represents a predetermined minimum volume of air to be inhaled to achieve the indication. In one embodiment, the electronic circuitry is housed in a unit which is removable from the remainder of the spirometer and therefore usable with different disposable spirometer components.

In accordance with another aspect of the present invention, an incentive spirometer is provided with an incentive interrupting mechanism which discourages improper breathing by the patient. In the preferred embodiments, this mechanism prevents an object in a vertical tube from rising in response to short inhalation bursts. It is preferred that the mechanism comprise a valve which is biased to open only in response to inhalation flow rates in excess of a threshold flow rate. The valve may be disposed on the object to be raised, in the tube in which the object is contained, or anywhere along the inhalation flow path. In each of these embodiments, the incentive goal can be obtained only in response to slow and prolonged inhalation efforts.

BRIEF DESCRIPTION OF THE DRAWINGS

The above and still further objects, features, and advantages of the present invention will become apparent upon consideration of the following detailed description of specific embodiments thereof, especially when taken in conjunction with the accompanying drawings, wherein:

FIG. 1 is a view in perspective of one embodiment of an incentive spirometer according to the present invention;

FIG. 2 is an exploded view in perspective of a portion of the spirometer of FIG. 1, modified to incorporate another feature of the present invention;

FIG. 13 is a view in perspective of a portion of still another embodiment of the incentive spirometer of the present invention;

FIG. 14 is a view in perspective and partial section of still another embodiment of the present invention wherein a nebulizer control arrangement is incorporated into the incentive spirometer;

FIGS. 15, 16, 17, and 18 are view in perspective of still further modified embodiments of the incentive spirometer having an incentive-interrupting feature of the present invention;

FIG. 19, 20, and 21 are views in perspective of still further respective embodiments of the present invention wherein the incentive-interruption feature is incorporated in a tube extending radially from the cylinder in which the object to be raised by inhalation is disposed;

FIGS. 22 and 23 are views in perspective of portions of still further modifications of the incentive-interrupting feature of the incentive spirometer of the present invention.

DESCRIPTION OF THE PREFERRED EMBODIMENTS

Figure 3:
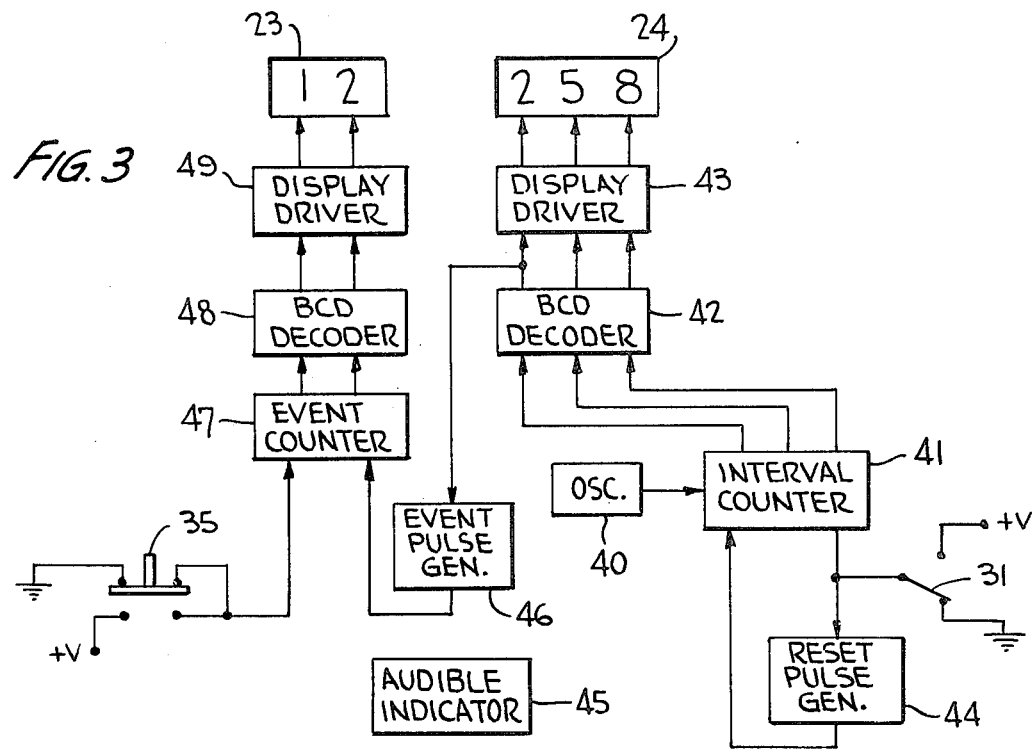
FIG. 3 is a functional block diagram of the electronic circuitry employed to record data associated with operation of the incentive spirometer of FIGS. 1 and 2.

Referring specifically to FIG. 1 of the accompanying drawings, there is illustrated an incentive spirometer of the type wherein the incentive for the patient is visually perceived by the patient in the form of an object raised in a transparent tube as a function of the patient's inhalation efforts. The incentive spirometer of FIG. 1 is conventional in all respects except for the provision of built-in means for recording the patient's efforts and means for interrupting the incentive when the patient improperly inhales in short bursts. The spirometer includes a base 10 which is in the form of a generally flat rectangular enclosure for a flow chamber. The top surface of base 10 is provided with an aperture 12 in which a valve 11 is slidably disposed to vary the portion of aperture 12 which is exposed to the ambient environment. In other words, valve 11 controls the size of the opening into the flow chamber via aperture 12. Another opening 13 into the flow chamber is defined in the front wall of base 10. A flexible hose 14 has one end connected to the flow chamber at opening 13 by means of a suitable fitting or clamp or the like. The other end of the flexible hose 14 terminates in a mouthpiece 15 adapted to be inserted into the mouth of a patient when the spirometer is in use.

A support member 16, having a generally inverted U-shaped configuration, is secured to base 10 with the ends of its vertically-extending legs 17 and 18 abutting the top surface of base 10. Legs 17 and 18 are hollow (or at least have flow passages vertically defined therein) and communicate with suitably provided openings 19 and 21, in the top surface of base 10. In this manner, the interior of legs 17 and 18 are in flow communication with the flow chamber enclosed within base 10. The horizontally-extending cross portion 22 of support member 16 serves as a housing for electronic circuitry employed to record the patient's inhalation efforts. An event-counter indicator 23 and a time indicator 24 are visible on the forward facing side of housing 22 along with a reset push-button 25. It should be noted that a buzzer, bell or other audible indicator may be provided in addition to or in place of the time indicator 24 for reasons discussed below.

Figure 4:
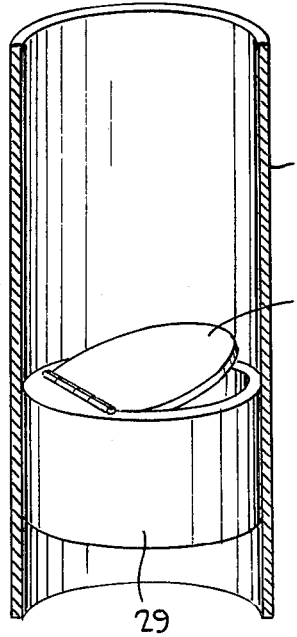
FIG. 4 is a view in perspective of a portion of the spriometer of FIG. 1 illustrating operation of the incentive-interrupting device.

A transparent vertically-extending tube 26 is secured between the vertically-extending legs 17 and 18 of support member 16. One end of tube 26 rests on the top surface of base member 10 while the other end abuts the underside of housing 22. The lower end of tube 26 is provided with one or more angularly extending openings 27 to permit admission of air into the bottom of the cylinder. Just above openings 27 there is disposed an annular flange 28 extending radially inward to serve as a seat for a generally cylindrical object 29 disposed in tube 26. Object 29 has a diameter slightly smaller than the diameter of the inside of tube 26 and is totally open at its lower end. The top of object 29 is closed except for a valve member 30 which, in the embodiment of FIG. 1, is in the form of a sector of the generally circular top surface of object 29 and which pivots along the chordal of the sector. Valve 30, which is illustrated in greater detail in FIG. 4, is biased closed by means of its hinged pivot arrangement. Alternatively, valve 30 may be fabricated of resilient plastic material which is constructed to bias the valve in its closed position. In either case, the valve is opened only if the force of in-rushing air through opening 27, acting on the underside of valve 30, is sufficient to overcome the bias to the closed position. As stated differently, valve 30 remains closed unless the mass flow rate of air upward through tube 26 exceeds some predetermined flow rate as determined by the bias force.

The closed top of tube 26 is provided with a suitable opening 35 (as seen in FIG. 2) to receive an actuator switch 31 depending from housing 22 and serving as part of the electronic circuitry disposed in that housing. Somewhat below the top of tube 26 there are provided two radially extending projections 32, 33 serving as flow passage connections between the interior of the cylinder and the hollow interiors of legs 17, 18, respectively of support member 16. It will therefore be appreciated that upon a suction being applied to mouthpiece 15, air from the ambient environment will be drawn through a flow path including openings 27, tube 26, connecting passages 32, 33, the hollow interiors of legs 17 and 18 of support member 16, the flow chamber enclosed within base 10, and flexible tubing 14. The flow rate of air through this path is a direct function of the suction or inhalation effort applied by the patient at mouthpiece 15. A parallel path is defined by aperture 12 into the flow chamber defined by base 10. If valve 11 is wide open, a stronger inhalation effort will be required on the part of the patient to raise object 29 since a considerable portion of the air inhaled by the patient will be shunted through aperture 12 rather than through the tube 26. As the opening provided by valve 11 is made smaller, a greater proportion of the inhaled air flows through tube 26, thereby requiring less effort by the patient to raise object 29. As indicated in FIG. 1, the various positions of valve 11 can be calibrated in flow rate required to achieve the incentive goal.

In-flowing air rising upward in tube 26 in response to an inhalation effort by the patient at mouthpiece 15 will cause object 29 to rise in tube 26. If the patient's inhalation effort is slow and gradual, as desired, object 29 will rise accordingly. It is the patient's goal, with this device, to cause the object 29 to rise to the top of the tube, where it contacts switch 31, and maintain the object at that position with as long an inhalation effort as possible. If the patient attempts to raise the object 29 with a sudden inhalation burst, the flow rate through tube 26 provides a force sufficient to open valve 30 so that a portion of the flow passes through the valve and object 29 drops to its position on seat 28.

If the patient achieves the goal of raising object 29 to contact switch 31, the switch actuates a timer which monitors the length of time during which object 29 contacts switch 31. This time is displayed at display unit 24 in hundredths of a second. In addition, actuation of switch 31 by object 29 increments the count at indicator 23 to provide a running count of the number of times the patient has achieved the goal of raising object 29 to the top of tube 26. This latter indication can be used by the therapist with the assurance that the patient has reached the desired goal with proper inhalation efforts. Switch 25 is a reset switch for the event counter and indicator 23. It is preferred that the count at indicator 23 be incremented only after the patient has maintained switch 31 actuated for a predetermined minimum period of time. This time is selected at the circuit of FIG. 3 in accordance with the minimum flow rate required through the unit for activation of the switch with object 29 so that inhalation of a predetermined minimum volume of air is achieved by the patient before a count is registered. A further signal, such as an audible sounding device or visible lamp, may be provided to indicate more dramatically to the patient that the predetermined minimum air volume has been inhaled. The therapist can, by adjusting valve member 11, change the volume of air associated with the predetermined switch actuation time.

The use of a cylindrical member or object 29 is similar in principle to the use of a sphere as in prior art incentive spirometers. In both cases, the incentive resides in observing the cylinder or sphere rise to a predetermined height in tube 26. The cylindrical object, however, is open at the bottom and the placement of valve 30 interrupts the incentive if the flow rate is too high through tube 26. Valve 30 has a sufficiently fast response time to allow an air burst to move directly through cylinder 29 rather than cause any substantial lifting of the cylinder. The valve 30 is preferably made of rigid polyvinyl chloride (PVC), the rigidity of which causes the valve to return to its closed position whenever the force on its underside, caused by the flowing air, falls below a pre-established threshold. The thickness and the rigidity of the valve material can be selected to provide the desired threshold flow rate to produce valve acutation.

In the embodiment illustrated in FIG. 1, base member 10, support member 16, flexible hosing 14, and mouthpiece 15 are sufficiently inexpensive to fabricate to render it practical to dispose of the entire spirometer after it has served its function for a particular patient. It may be desirable, however, to preserve the electrical components used for recording the inhalation efforts for re-use with disposable portions of other spirometers. An embodiment including these features is illustrated in FIG. 2 to which specific reference is now made. Specifically, the component housing portion 22a is shown to be selectively removable from the tops of vertically-extending legs 17 and 18. Housing 22a, which constitutes the horizontal crosspiece portion of the inverted U-shaped support member 16, is provided with a plurality of latching members 36 which are pivotable to engage latching pins 37 projecting radially outward from legs 17 and 18. In addition, the upper surfaces of legs 17 and 18 are provided with locator pins 38 or the like which mate with locator recesses (not shown) in the underside of housing 22a. In order to remove housing 22a from the disposable portion of the spirometer, latches 36 are disengaged from pins 37 and the housing 22a is simply lifted off the spirometer. In order to deploy housing 22a with a spirometer, it is simply placed over the top of legs 17, 18 until the guide pins 38 mate with the suitably provided recesses and switch 31 extends through access hole 35 in the top of cylinder 26. It will be apparent that a variety of structural arrangements may be provided in order to render the electronic components removable from the disposable portion of the spirometer and that the particular construction illustrated in FIG. 2 is provided as merely one example of this feature.

The electrical circuitry contained within housing 22 or 22a is illustrated diagrammatically in FIG. 3. The illustrated circuitry is powered by a battery contained within the housing. An interval counter 41 is arranged to count pulses from an oscillator 40 having a frequency of 100 Hz. The output count from counter 41, in binary form, is applied to a binary coded decimal decoder 42 which converts the binary code into BCD format for application to display driver circuits 43. These display driver circuits drive the time indicator 24 to provide a readout in hundredths of a second.

The start count signal for enabling counter 41 to count the pulses from oscillator 42 is derived from the contact switch 31 which is actuated when member 29 contacts this switch at the top of tube 26. Switch 31 is shown schematically in FIG. 3 in its OFF position and is seen to provide a positive voltage for the interval counter, when actuated, to initiate counting.

A reset pulse generator 44 also receives the start count pulses from switch 31 and applies them to the interval counter 41 to reset that counter before counting is initiated.

An event pulse generator 46 is connected to the BCD format count signal at the output of decoder 42 to provide one output pulse for each activation of actuator switch 31. For example, the event pulse generator 46 may comprise the RCA CD4047B low-power monostable/astable multivibrator and RCA CD40198B AND-OR gate. In the connection illustrated in FIG. 3, the event pulse generator provides its output pulse only if switch 31 is actuated for one second, the connection being determined by which output line or lines from decoder 42 is utilized to drive the event pulse generator. This one second duration is entirely arbitrary and ca be changed by selecting any one of the other output leads from decoder 42 to trigger the event pulse generator. For example, with appropriate gating and connection to the decoder output leads, a one-half second duration of switch 31 may be required before the event pulse generator 46 provides its output pulse. Whichever time period is chosen, that period represents, for each setting of valve member 11, a respective minimum volume of air inhaled by the patient. Specifically, since the minimum flow rate required to activate switch 31 can be calibrated for each valve setting, that flow rate multiplied by the selected time yields the minimum inhaled volume. The selected time is therefore proportional to different minimum volumes selected at the valve member 11. After the selected time expires at the event pulse generator, a pulse is applied to an audible indicator 45 and an event counter 47 which counts these pulses. The binary output count from event counter 47 is converted into BCD format by decoder 48. The counter BCD code drives the display drivers circuits 49 which feed the event count indicator 23. Therefore, event count indicator 23 registers the number of times that actuator switch 31 has been actuated for at least a predetermined time, for example, one second. If it is desired to reset the count in event counter 47, this may be done by depressing reset switch 25. Display units 23 and 24 are preferably liquid crytal display units which draw relatively small amounts of current. The electronic circuitry may be embodied in an integrated circuit so that the entire arrangement may be housed in a relatively small space.

It should be noted that the indication in display unit 24 of the length of time during which the achievement has been effected permits a simple calculation to be used to determine the air displacement volume during an inhalation period. Specifically, if valve 11 is calibrated in terms of the mass air flow rate required to lift member 29, a simple multiplication of that mass flow rate times the recorded time provides a measure of the air displacement volume.

Figure 5:
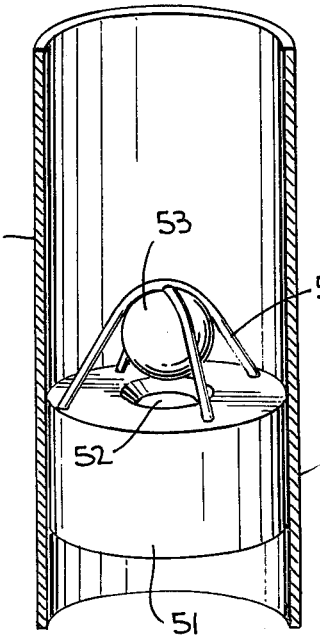
FIGS. 5, 6, 7, and 8 are views in perspective, similar to FIG. 4, showing different respective versions of the incentive-interrupting mechanism.

It should be noted that a particular valve 30 illustrated in FIGS. 1 and 4 for interrupting the incentive during spirometer operation is only one example of numerous types of mechanisms which can be employed to the same end. For example, and reference is made to FIG. 5, the object to be raised in tube 26 may take the form of a cylinder 51 which, like cylinder 29, is open at its bottom. Cylinder 51 is closed at its top except for an annular opening 52 disposed generally centrally of that top. A sphere 53, having a diameter slightly larger than the diameter of aperture 52, is trapped atop cylinder 51 by a cage-like structure 54. Cage-like structure 54 permits vertical movement of the ball 53 sufficient to unblock aperture 52 in the event that a force of sufficient magnitude to lift sphere 53 is applied to the underside of the sphere through aperture 52. It will be appreciated that if the inhalation effort is a short burst, with an air flow of sufficient magnitude to raise sphere 53 off of its seat in aperture 52, member 51 will not rise in tube 26 in response to that inhalation. Since it is the weight of sphere 53 which determines the force required to unseat that sphere from aperture 52, the mass flow rate required to unseat this sphere can be readily calculated.

Figure 6:
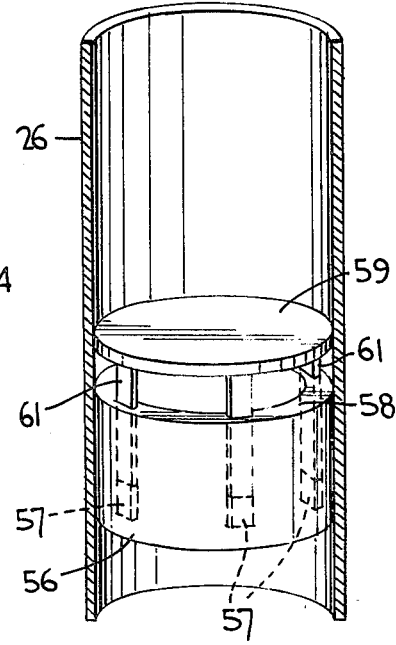

Another form of incentive-interrupting mechanism built into the object to raised is illustrated in FIG. 6. A hollow cylinder 56, open at both its ends, is disposed longitudinally in cylinder 26. A plurality of angularly spaced bores 57 are defined longitudinally in the cylinder 56 from its top edge 58. A cap member 59 is provided with a plurality of depending pin members 61 proximate the periphery of the cap member and positioned in correspondence with the positions of bores 57. The lower extremities of pins 61 are provided with flanges so that the pins are retained captive within bores 57 but are free to slide longitudinally therein. Normally, the weight of cap 59 forces pins 61 fully into bores 57 so that cap 59 sits atop edge 58 of cylinder 56. A low slow inhalation effort permits cylinder 56 to be raised in tube 26 without raising cap 59 off edge 58. A sudden inhalation burst, however, raises cap 59 and precludes lifting of cylinder 56 into tube 26. Again, the weight of cap 59 can be selected to permit opening of the cap valve arrangement at the desired mass flow rate of air through tube 26.

Figure 7:
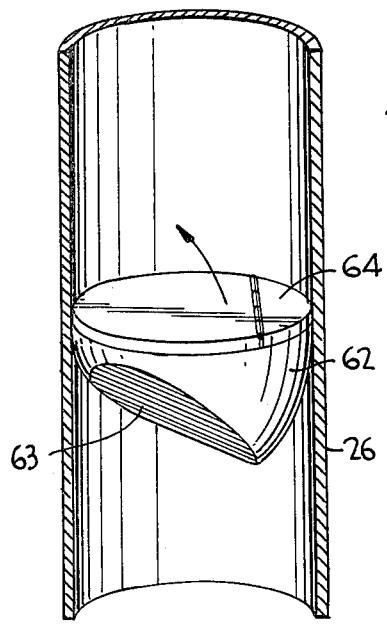

Referring now to FIG. 7, the object 62 to be raised in tube 26 takes the form of a hollow cylinder 62 having its bottom edge 63 truncated obliquely so that the cylinder is longer on one side than on the other. The top of the cylinder is closed except for a valve 64, similar to valve 30 in the embodiment of FIG. 4. Member 62 tends to rise readily in tube 26 when a proper gradual inhalation effort is executed. However, in response to a short inhalation burst, member 62 has a tendency to rotate counterclockwise (as referenced to FIG. 7) causing member 62 to bind along the inner wall of cylinder 26. When the object 62 becomes stuck, vent 64 opens to avoid a sudden stop in the inhalation exercise; however, the visual reward provided by the rising of object is inhibited.

Figure 8:
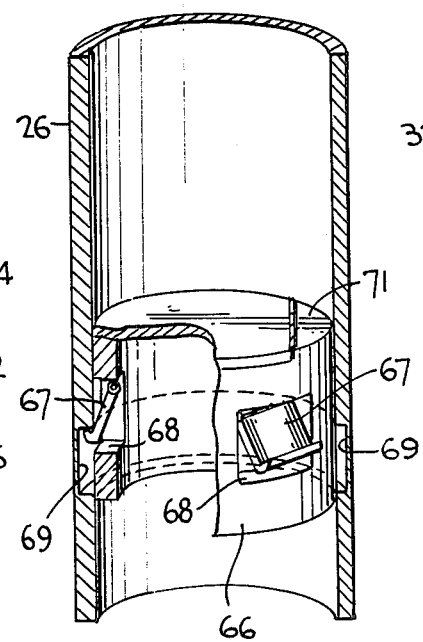

The embodiment of FIG. 8 includes, as the object to be raised, a hollow cylinder 66 which is open at its bottom and closed at its top. A plurality of angularly spaced apertures 68 are defined in the wall of cylinder 66 and each is covered by a flap 67 which is hinged along its upper edge. Preferably, the flaps are disposed in recessed sections of cylinder 66 as shown. A sudden inhalation burst causes the flaps to open, forcing the lower parts of the flaps radially outward from the cylinder 66. The flaps 67 thus catch on irregularities 69, such as a recess or projection, formed in tube 26 and prevent further upward movement of cylinder 66. A valve 71 may be provided along the top side of cylinder 66 and arranged to open in the event that the cylinder does become stuck in tube 26 so as to avoid a sudden termination of the inhalation exercise effort by the patient.

Figure 9:
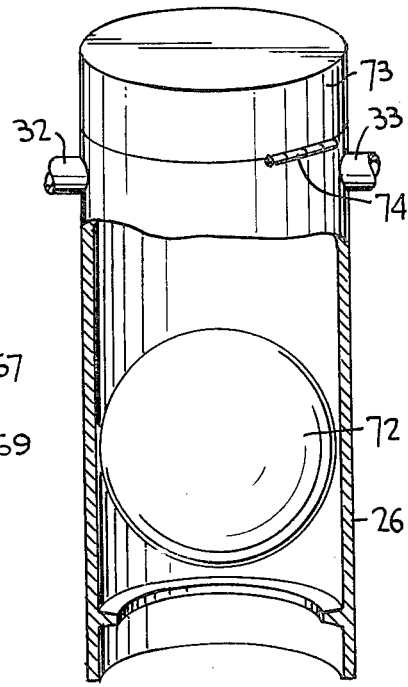
FIG. 9 is a view in perspective of a portion of another incentive spirometer embodiment wherein the incentive-interrupting feature is disposed in the cylindrical tube.

In the embodiment of FIG. 9, the top end of tube 26 is open and the object to be raised in the tube is in the form of a sphere 72. The incentive-inhibiting mechanism in this embodiment is a hinged venting valve 73 disposed proximate the top of tube 26. Specifically, valve 73 is in the form of a disc hinged at 74 along a portion of its periphery so as to be biased to a closed position, as illustrated, wherein it blocks air flow into the top of tube 26. If the inspiration air flow rate is too great, as would be caused by a sudden inhalation burst, vent valve 73 pivots downward to permit air to enter the top of open tube 26 and be drawn by the inhalation suction through passages 32 and 33 into the longitudinally-extending flow paths 17 and 18. This, in effect, provides a short-circuit around sphere 72 which experiences a considerably smaller lifting flow than that actually being inhaled by the patient. Sphere 72, as a result, does not rise in tube 26 and the incentive is interrupted.

Figure 10:
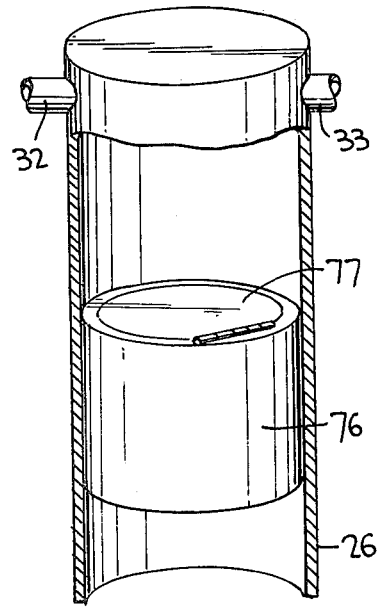
FIG. 10 is a view in perspective of a portion of another embodiment of the incentive spirometer of the present invention.

The embodiment of FIG. 10 employs a similar type of vent valve 77; however, the valve 77 is disposed at the top of a cylinder 76 which is the object to be raised in tube 26. Tube 26, in this embodiment, is closed at the top. Vent valve 77 is arranged to pivot upwardly in response to an inhalation burst flowing through the open end of hollow 76 to thereby prevent further lifting of cylinder 76 in the tube.

Figure 11:
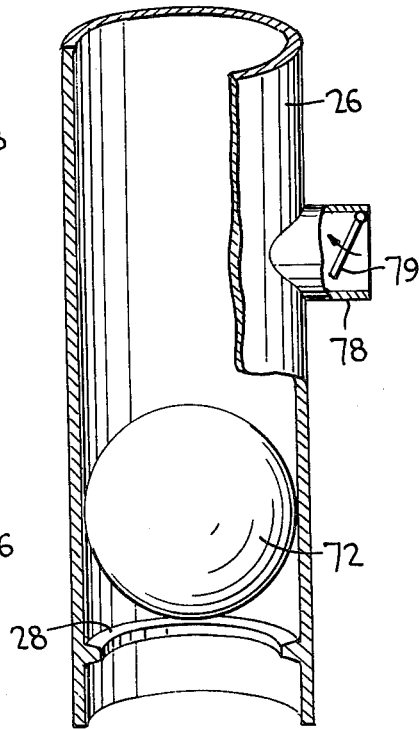
FIG. 11 is a view in perspective of a portion of another embodiment of the present invention.

In FIG. 11, the incentive-inhibiting device takes the form of a valve 79 disposed in a tube 78 extending radially from tube 26 at a location above the object to be raised by the inhalation effort. A sudden inhalation burst by the patient causes valve 79 to pivot inward into tube 78 permitting ambient air to rush into tube 26 at a location above the object to be raised. This free supply of air via tube 78 precludes lifting of the object in tube 26 and inhibition of the incentive to the patient.

Figure 12:
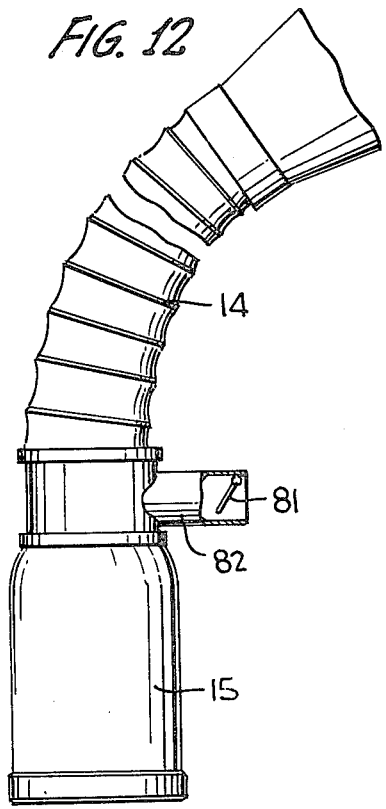
FIG. 12 is a view in perspective of a portion of another embodiment of the present invention wherein the incentive-interrupting feature is incorporated in the tube feeding the mouthpiece of the incentive spirometer.

A similar concept is illustrated in FIG. 12 wherein the valve for short-circuiting the air flow around the object to be lifted in tube 26 is disposed at the juncture between flexible tubing 14 and mouthpiece 15. Specifically, the valve 81 is disposed at the terminal end of a tubular passage 82 extending radially outwardly from flexible tube 14. A sudden inhalation burst by the patient at mouthpiece 15 results in valve 81 pivoting inward to permit ambient air to rush into the mouthpiece and reduce the suction applied via flexible tube 14 to the tube 26.

It should be noted that a bias vent for preventing the incentive object to be lifted can be located anywhere in the flow path. For example, in FIG. 13 the valve 83 is arranged at the very top of tube 26 serving as a cover for that tube. In response to a short inhalation burst, valve 83 pivots downward into the tube to permit air from the surrounding region to enter the tube and thereby reduce the effective suction applied to the bottom of the tube so that the air flow through the tube is reduced below that required to lift sphere 72.

The embodiment illustrated in FIG. 14 illustrates a nebulizer 84 in the flow path upstream of flexible tube 14. A tube 86 projects radially from the flow path and is terminated with a valve 87 which is drawn inward of tube 86 in response to an inhalation burst by the patient at mouthpiece 15. This embodiment of FIG. 14 is similar to the embodiment of FIG. 13 but serves the additional function of preventing medication in nebulizer 84 from being inhaled in a burst. Specifically, the venting valve 87, disposed between nebulizer 84 and flexible tube 14, provides a short-circuit actuated by a sudden burst of inhalation and is useful for any nebulizer whether or not it is part of an incentive spirometer system.

FIG. 15 illustrates another form of incentive-inhibiting mechanism built into the object to be raised in tube 26. Specifically, the object to be raised is a cylinder 88, open at its bottom, and having its interior contoured to provide an hour-glass shaped flow path extending longitudinally through its interior. A sphere 89 is disposed in the upper portion of the hour-glass passage and has a larger diameter than the narrow midportion of that passage so as to block the flow therethrough in its normal at-rest position. The top of cylinder 88 is provided with a plurality of cross members 91 providing a cage which prevents removal of sphere 89 from the interior of cylinder 88. A sudden burst of inhalation causes sphere 89 to unseat from its illustrated position to permit air to flow through the cylinder and thereby preclude lifting thereof. A long slow inhalation, on the other hand, does not unseat the sphere 89 and lifts the cylinder 88 in the tube 26.

The embodiment of FIG. 16 includes sphere 72 as the object being raised in tube 26. The incentive-inhibiting device is a butterfly valve 92, pivotable about an axis 93 disposed at the very top of tube 26. Sudden inhalation bursts by the patient result in valve 92 pivoting about axis 93 to permit ambient air to enter through the top of tube 26. In this manner similar to the embodiments described above, this in-rushing air severely reduces the air flow entering from the bottom of the tube and prevents sphere 72 from rising in response to the inhalation bursts.

The embodiment of FIG. 17 illustrates a butterfly valve 95, pivotable about an axis 96, disposed at the top of a hollow cylindrical object 94 to be raised in tube 26. In this embodiment, the top of tube 26 is closed and the valve 95 operates to perform the same function as valve 30 in FIG. 4.

Referring to FIG. 18, the incentive-inhibiting mechanism is shown in another embodiment as part of the object being raised in tube 26. The object is a hollow cylinder 97 having an annular shoulder 98 disposed concentrically therein at some predetermined longitudinal location. A support in the form of cross-members 102 is disposed across the top of cylinder 97 in a manner so as to permit air flow through the top of the cylinder. A disc-like valve member 99 is supported from support member 102 by a compression spring 101 which urges the valve member against shoulder 98. In operation, a burst of inhalation sufficient to overcome the bias force of spring 101 will displace the valve member 99 from its seat on shoulder 98 to permit the inspiration air to flow through cylinder 97 and thereby preclude lifting of the cylinder. Inhalation flow rates below that necessary to overcome the force of spring 101 results in the cylinder being lifted in tube 26.

A similar type of valve arrangement is illustrated in FIG. 19, but not included as part of the object being raised. Instead, there is a tube 103 projecting radially from the cylinder 26 at a location above the normal rest position of the object 72 to be raised. An annular shoulder 104 is disposed in radially-extending tube 103 concentrically about the central longitudinal axis of that tube. A valve member 106 in the form of a disc having a larger diameter than the opening in shoulder 104 and disposed on the tube 26 side of shoulder 104. A rod 107 extends perpendicularly from disc 106 in a generally axial direction in tube 103 and is biased by spring 108 to draw disc 106 to its closed position (toward the left as illustrated in FIG. 18). If the suction in tube 26, resulting from an inhalation burst is sufficiently great, disc 106 is displaced against the biasing action of the spring 108 to permit air to flow through tube 103 and the opening in shoulder 104 into tube 106. This air, in the manner described above for other embodiments, acts to short-circuit air flow from below sphere 72 and prevents the sphere from being raised in the tube.

The embodiment illustrated in FIG. 20 is similar to that illustrated in FIG. 19 except that the annular shoulder 109 is disposed at the end of the tube 114 projecting radially from tube 26 at a location above object 72 to be raised. A disc-like valve member 111 is biased into its seated position on shoulder 109 by means of a spring 112 disposed about a rod 113 connected to the disc 111.

Still another embodiment of a similar type is illustrated in FIG. 21 wherein a tube 116 projects radially from tube 26 and includes a butterfly-type valve 117 pivotable about an axis 118 disposed diametrically across tube 116. The butterfly valve is rotatable in response to a sudden inhalation burst to permit air to enter tube 26 via tube 116 at a location above sphere 72.

In the embodiment of FIG. 22, the incentive-inhibiting mechanism is disposed at the top of tube 26. The top of tube 26 is fitted with a frusto-conical cap 119 disposed coaxially with respect to tube 26 with its smaller diameter end projecting downward into the tube. The larger diameter end of the frusto-conical member 119 is provided with an annular cover 121. The opening in annular cover 121 is normally covered with a disc-like member 122 secured to an actuator rod 123 which extends downward from disc member 122 and is slidable through the open smaller diameter end of the member 119. A compression spring 124 is secured about shaft 123 and has its end secured to disc member 122 and the lower end of member 119. Sudden bursts of inhalation by the patient, reflected at passages 32 and 33 via passages 17 and 18, cause a suction which draws disc member 122 downward against the biasing force of spring 124. Disc member 122 is thus drawn away from the opening in annular cover 121 to permit air to enter tube 26 via suitably provided openings in frusto-conical member 119. In this manner, the air flow from below sphere 72 is considerably reduced and the sphere does not rise in tube 26.

In another embodiment illustrated in FIG. 23, the same valve illustrated in FIG. 21 is incorporated into a cylinder 126 to be raised by the inhalation efforts of the patient. Operation of the valve disposed within cylinder 126 proceeds in the same manner as that described in relation to FIG. 21, except that the inhalation effort causes air flow through cylinder 126 to force the disc member 122 upward and away from annular shoulder 121 so that air can flow through the cylinder 126. The bias afforded by spring 124 assures that the disc member 122 is raised only in response to undesirable inhalation bursts.

The invention has been described in terms of the flow-type spirometer as opposed to a volume-type spirometer. It will be appreciated that the valving arrangements described herein as part of base 10 can readily be used for volume-type spirometers because of the inherent ability of the present invention to measure the flow rate of air through a known volume for a given period of time. Further, varying the flow rate (by valve 11 or the like) required to achieve actuation of the incentive switch for the predetermined time period results in a corresponding variation of the minimum volume of air inhaled during that period.

While, we have described and illustrated several specific embodiments of our invention, it will be clear that variations of the details of construction which are specifically illustrated and described herein, may be resorted to without departing from the true spirit and scope of the invention as defined in the appended claims.

We claim:

1. An incentive spirometer comprising:
   a flow path through which a patient can inhale air;
   means responsive to air flow in said flow path for providing a visually-perceptible incentive indication for the patient; and
   inhibiting means responsive to inhalation suction force above a predetermined force for inhibiting said incentive indication.

2. The spirometer according to claim 1 wherein said inhibiting means comprises a valve which is biased closed and is opened by said suction force above the predetermined suction force.

3. The spirometer according to claims 1 or 2 further comprising built-in indicator means for registering an indication each time the patient inhales a predetermined volume of air without exceeding said predetermined suction force.

4. The spirometer according to claims 1 or 2 further comprising built-in indicator means for displaying the time duration of each patient's inhalation exceeding said predetermined volume of air without exceeding said predetermined suction force.

5. A method for encouraging proper inhalation exercises in an incentive spirometer, said method comprising the steps of:
   providing a visually-perceptible incentive indication for a patient to inhale air; and
   inhibiting said incentive indication in response to rapidly applied suction forces by the patient during inhalation.

6. The method according to claim 5 further comprising the step of providing an indication each time the patient inhales a predetermined volume of air without exceeding a predetermined mass flow rate of that air.

7. The method according to claim 6 further comprising the step of displaying the time duration of each patient's inhalation in which said predetermined volume of air has been inhaled without exceeding said predetermined mass flow rate.

8. An incentive spirometer comprising:
   an inhalation flow path through which air flows in response to an inhalation suction force applied thereto by a patient;
   a transparent column disposed in said inhalation flow path such that inhaled air flows therethrough with at least one flow component directed vertically upward;
   incentive member means disposed in said column for rising in said column in response to inhalation air flow above a predetermined low flow rate through said column; and
   incentive-inhibiting means responsive to air flow above a predetermined high flow rate in said flow path for preventing said incentive member means from rising in said column.

9. The incentive spirometer according to claim 8 wherein said incentive member means and said incentive-inhibiting means comprise a hollow member open at its bottom and closed at its top by valve means, said valve means being responsive to a predetermined force applied thereto from within said hollow member for opening the top of said hollow member to permit air flow in said column to flow through said hollow member and thereby prevent lifting of said hollow member in said tube, said predetermined force corresponding to said predetermined high flow rate flowing in said column.

10. The incentive spirometer according to claim 9 wherein said valve means comprises a resiliently-biased flapper valve.

11. The incentive spirometer according to claim 9 wherein said valve means comprises a ball valve wherein the closed top of said hollow member is provided with an annular opening and a ball member which normally sits in said annular opening above said closed top of said hollow member, said valve means further comprising retention means for retaining said ball in a predetermined volume above said hollow member.

12. The incentive spirometer according to claim 9 wherein said valve means comprises the entire top of said hollow member, said top including depending means slidably retained in said hollow member to permit vertical displacement of said top with respect to said hollow member in response to predetermined upward forces acting on said top from within said hollow member.

13. The incentive spirometer according to claim 9 wherein said valve means comprises a butterfly valve pivotable about an axis extending substantially perpendicular to the direction of flow in said column.

14. The incentive spirometer according to claim 8 wherein said incentive member means has a flow path defined therethrough and said incentive-inhibiting means comprises valve means normally biased to close said flow path, said valve means being responsive to a predetermined upward force applied thereto from within said flow path for opening said flow path to permit air flow in said column to flow through said flow path and thereby preclude rising of said incentive member means in said column, said predetermined force corresponding to air flow rate in said column exceeding said predetermined high flow rate.

15. The incentive spirometer according to claim 14 wherein said valve means is a ball valve.

16. The incentive spirometer according to claim 14 wherein said valve means is a butterfly valve.

17. The incentive spirometer according to claim 14 wherein said valve means is a resiliently biased flapper valve.

18. The incentive spirometer according to claim 14 wherein said valve means comprises:
an apertured wall disposed within said incentive member means substantially perpendicular to the direction of flow through said column;
a closure member; and
means for spring biasing said closure member downward against said apertured wall to preclude flow through said apertured wall in said incentive member means.

19. The incentive spirometer according to claim 8 wherein said incentive-inhibiting means comprises an object which is aerodynamically contoured to rotate about a substantially horizontal axis in response to flow rates through said column in excess of said predetermined high flow rate.

20. The incentive spirometer according to claim 8 wherein said incentive member means comprises a hollow member open at its bottom and closed at its top and including radially outward expansible means which project outwardly to engage said column in response to a predetermined presure inside said hollow member.

21. The incentive spirometer according to claim 8 wherein said incentive-inhibiting means comprises valve means responsive to a predetermined suction pressure applied to said column during an inhalation exercise for admitting ambient air into said column at a location in said column above said incentive member means.

22. The incentive spirometer according to claim 21 wherein said valve means is disposed at the top of said column.

23. The incentive spirometer according to claim 22 wherein said valve means is a butterfly valve which is rotatable about an axis disposed generally perpendicular to the direction of flow in said column.

24. The incentive spirometer according to claim 22 wherein said valve means comprises a spring-loaded valve having a movable valve member and a spring member which biases said movable valve member in a generally upward direction.

25. The incentive spirometer according to claim 22 wherein said valve means comprises a resiliently biased flapper valve.

26. The incentive spirometer according to claim 21 further comprising a flow passage communicating between the ambient environment and a location in said column above said incentive member means at rest, and wherein said valve means is disposed in said flow passage.

27. The incentive spirometer according to claim 8, wherein said inhalation flow path includes a flexible tube and a mouthpiece through which a patient inhales when the spirometer is in use, and wherein said incentive-inhibiting means comprises valve means communicating between the ambient environment and the interior of said flexible tube for permitting ambient air inflow into said flexible tube in response to air flow through said flexible tube above said predetermined high flow rate.

28. The incentive spirometer according to claim 8 further comprising indicator means for registering an indication each time said incentive member means is raised to a predetermined height in said column.

29. The incentive spirometer according to claims 8 or 28 further comprising built-in timing means for counting and displaying the time duration during which said incentive member means is raised to a predetermined height in said column.

* * * * *